United States Patent [19]

Peterson et al.

[11] Patent Number: 5,476,207
[45] Date of Patent: * Dec. 19, 1995

[54] METHOD AND APPARATUS FOR FLUXING AND SOLDERING TERMINALS ON A PRINTED CIRCUIT BOARD

[75] Inventors: John P. Peterson, Chapel Hill; Paul Brinkley, Morrisville, both of N.C.

[73] Assignee: Northern Telecom Limited, Montreal, Canada

[*] Notice: The portion of the term of this patent subsequent to Nov. 21, 2012, has been disclaimed.

[21] Appl. No.: 345,681

[22] Filed: Nov. 21, 1994

[51] Int. Cl.⁶ .......................... B23K 31/02; B23K 31/12
[52] U.S. Cl. .................. 228/102; 228/180.1; 228/223; 228/37
[58] Field of Search .................. 228/223, 37, 180.1, 228/102, 105, 9

[56] References Cited

U.S. PATENT DOCUMENTS

| | | | |
|---|---|---|---|
| 4,890,781 | 1/1990 | Johnson et al. | 228/37 |
| 5,238,171 | 8/1993 | Takahashi | 228/105 |
| 5,332,145 | 7/1994 | Bell et al. | 228/223 |

*Primary Examiner*—P. Austin Bradley
*Assistant Examiner*—Jeffrey T. Knapp
*Attorney, Agent, or Firm*—Foley & Lardner

[57] ABSTRACT

Fluxing and soldering terminals on a printed circuit board by an in-line process in which flux concentration is determined at specific locations laterally of the passline. At each of the positions infrared light is passed through a wall of flux which is being directed at the board. The infrared light becomes partly absorbed by materials in the flux and the unabsorbed light which passes through the wall of flux is used to generate signals corresponding to the different wavelengths of unabsorbed light at each of the locations. This enables a determination to be made of the flux concentration at each location. The signals are preferably used to effect a change in the flow rate of flux at any specific location so as to control the amount of flux deposited upon the board. Particularly useful for "no-clean" flux applications.

17 Claims, 4 Drawing Sheets

METHOD AND APPARATUS FOR FLUXING AND SOLDERING TERMINALS ON A PRINTED CIRCUIT BOARD

This invention relates to methods and apparatus for fluxing and soldering terminals on a printed circuit board.

In the manufacture of printed circuit boards in which soldering at terminal positions on the boards is performed by known wave soldering techniques in an in-line process, soldering flux is sprayed onto the board undersurfaces in a fluxing station, the boards then proceeding through at least one preheating station before being subjected to the solder wave. Quality control of such a process is essential not only to maintain required competitive quality of the final product, but also to minimize wastage which may be extremely expensive to the board manufacturer. For quality control purposes, it is practical only to select boards at intervals for test purposes to determine whether the soldering process is proceeding in the desired manner. However, there is an inordinate time taken to test any particular board completely, e.g. perhaps up to a two-day period for functional testing, and during this time succeeding boards are being manufactured upon the same wave soldering apparatus. Where a functional problem is discovered and this is the result of some soldering inadequacy, because for instance, of some inadvertent change in machine operation, in flux application or in solder application, then all these succeeding boards will suffer the same problems as the board being tested and may be below acceptable standards and therefore scrapped. As is well known, product rejection may therefore be extremely expensive and operationally inconvenient to a manufacturer.

The present invention seeks to provide a method and apparatus for fluxing and soldering terminals on a printed circuit board in which the above problems are minimized.

Accordingly, the present invention provides according to one aspect, a method of fluxing and soldering terminals on a printed circuit board comprising: moving the printed circuit board along a passline through a flux application station while directing a wall of flux across a surface of the board; in each of a plurality of locations spaced laterally of the passline, passing infrared light having a range of wavelengths, through the wall of flux to cause different wavelengths of the infrared light to be absorbed at least partially by different materials in the flux; receiving the unabsorbed infrared light which has passed through the wall at each of the locations; for each location, generating signals corresponding to the different wavelengths of unabsorbed infrared light at that location to enable a determination to be made of the flux concentration at that location; and moving the board carrying the flux on said surface towards and through a solder application station to apply solder to the terminals.

With the method according to the invention defined above, not only may the flux concentration at any location be determined, but also the flux distribution across the board may be determined. Where a flux distribution across the board is found to be undesirable in that it may possibly result in soldering problems which are visual or lead to functional problems, operation of the apparatus may be immediately stopped until the undesirable flux pattern has been eliminated.

The infrared light which is transmitted may be a collimated beam, but this inherently has a high loss of energy before reception of the unabsorbed light. Conveniently therefore, the infrared light is focused upon a position within the wall of flux and the unabsorbed light emerges from the wall and is divergent from the focal point. Focusing results in less energy loss and the light may be transmitted for greater distances between transmitted and received positions than collimated light. This is a practical consideration because lenses used for transmitting and receiving the infrared light need to be sufficiently far apart and away from the wall of flux so as not to be coated by the flux.

In the above method, infrared light may be transmitted and received and signals generated at each location simultaneously. Alternatively, this procedure may be followed in some predetermined order across the passline. In a further alternative, infrared light is transmitted from a transmission position which is moving laterally of the passline, the unabsorbed light being received at a reception position locked in phase with the transmittal position. Thus, generated signals may be obtained at any of an infinite plurality of locations across the passline and the flux concentration determined at that location.

It is also possible to use the signals which are generated and corresponding to the different wavelengths of the unabsorbed light to effect operation of control means for the flux flow application within certain limits. With such a method, the flux flow concentration at any location may thus be changed towards that desired to achieve the desired flux concentration.

Accordingly, the present invention further provides a method of fluxing and soldering terminals on a printed circuit board comprising: moving the printed circuit board along a passline through a flux application station while directing a wall of flux across a surface of the board; in each of a plurality of locations laterally of the passline, passing infrared light having a range of wavelengths, through the wall of flux to cause different wavelengths of the infrared light to be absorbed at least partially by different materials in the flux; receiving the unabsorbed infrared light which has passed through the wall at each of the locations; for each location, generating signals corresponding to the different wavelengths of unabsorbed infrared light at that location and thus corresponding to the actual flux concentration at that location, and when the signals differ from a datum signal which corresponds to the desired flux concentration at that location, effecting a change in flow of flux to change the actual flux concentration towards that desired; and moving the board carrying the flux on said surface towards and through a solder application station to apply solder to the terminals.

The invention further includes a wave soldering apparatus comprising a flux application station, and a solder application station disposed downstream of the flux application station along a passline for printed circuit boards to be passed through the apparatus; means for creating a wall of flux in the flux application station and for directing the wall of flux upwardly towards the passline to coat with flux printed circuit boards as they move through the application station; means for passing infrared light at a plurality of locations spaced laterally of the passline, through the wall of flux and means for receiving infrared light which is unabsorbed by materials of the flux in the wall and which has passed through the wall, the infrared light having an operating range of wavelengths; and means for generating signals corresponding to the different wavelengths of unabsorbed light at each of the plurality of locations to enable a determination to be made of the flux concentration at that location.

The invention also includes a wave soldering apparatus comprising a flux application station, and a solder application station disposed downstream of the flux application station along a passline for printed circuit boards to be passed through the apparatus; means for creating a wall of flux in the flux application station and for directing the wall of flux upwardly towards the passline to coat with flux printed circuit boards moving through the application station; means for adjusting the flux concentration to any of a plurality of locations spaced laterally of the passline; means for transmitting infrared light through the wall of flux at each of the plurality of locations and means for receiving infrared light which is unabsorbed by the materials of the flux in the wall and which has passed through the wall, the infrared light having an operating range of wavelengths; means for generating signals corresponding to the different wavelengths of unabsorbed light at each of the locations, the generated signals also corresponding to actual flux concentrations at that location; and means to effect a change in the flux concentration at any of the locations towards a desired flux concentration when a generated signal at that location differs from a datum signal which corresponds to the desired flux concentration.

Embodiments of the invention will now be described, by way of example, with reference to the accompanying drawings, in which.

Figure 1:
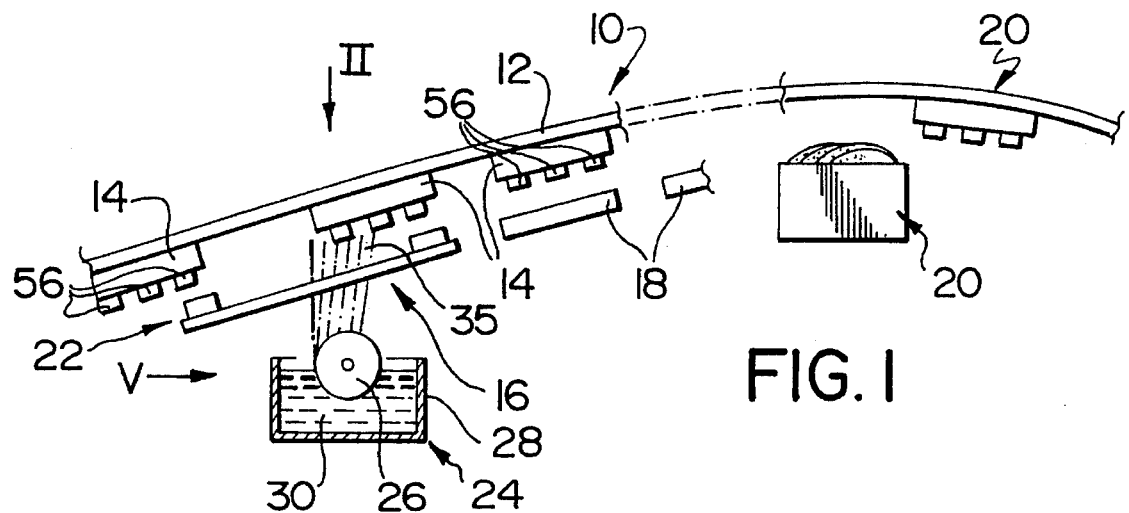
FIG. 1 is a diagrammatic side elevational view of a wave soldering apparatus showing printed circuit boards being fed therethrough.
Figure 2:
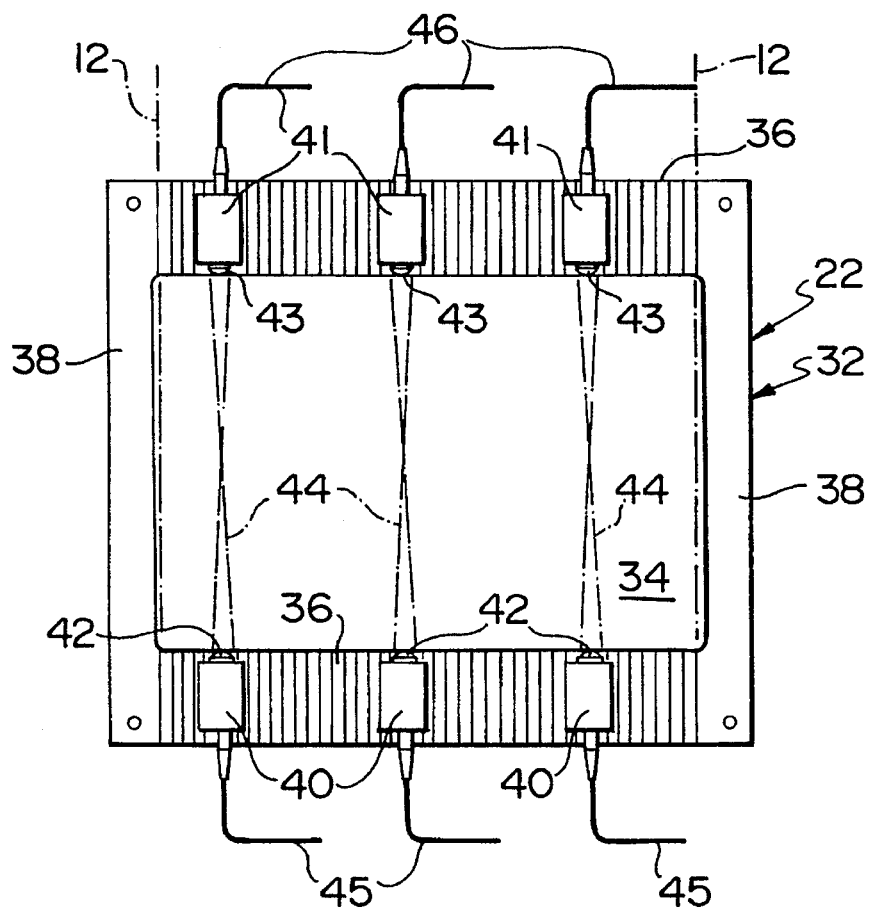
FIG. 2 is a plan view in the direction of arrow II in FIG. 1 of part of the wave soldering apparatus and to a larger scale.
Figure 5:
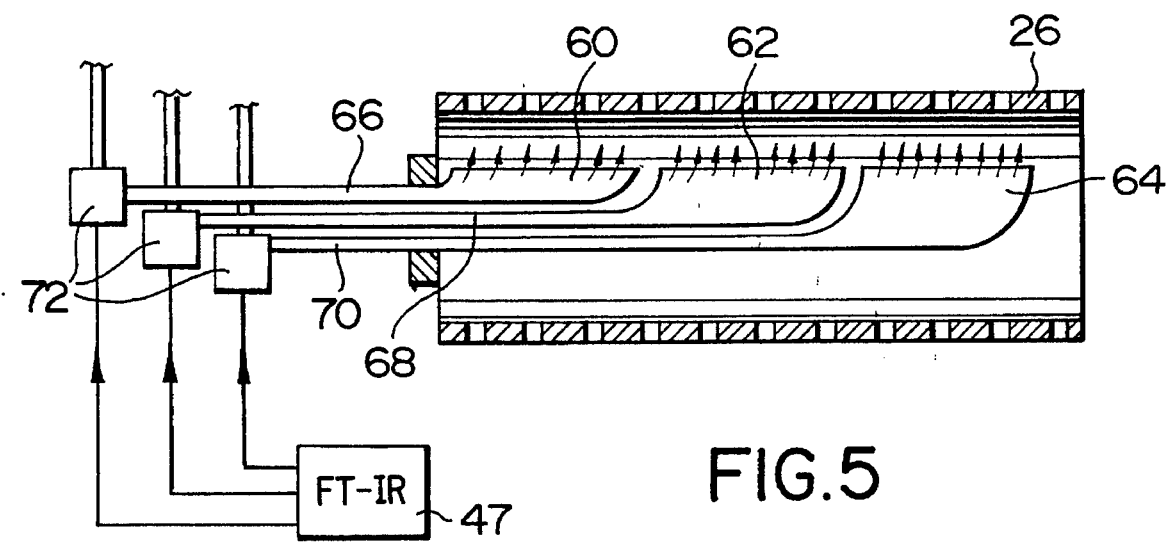
Figure 6:
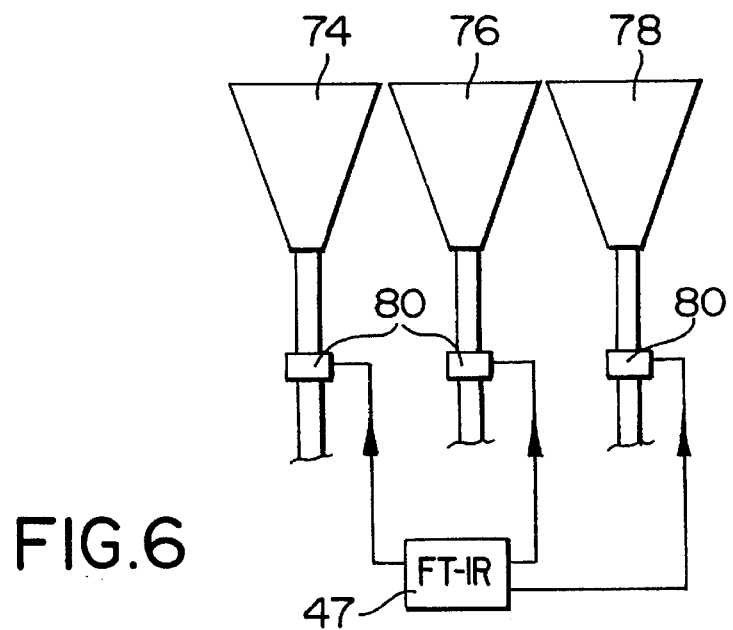
Figure 7:
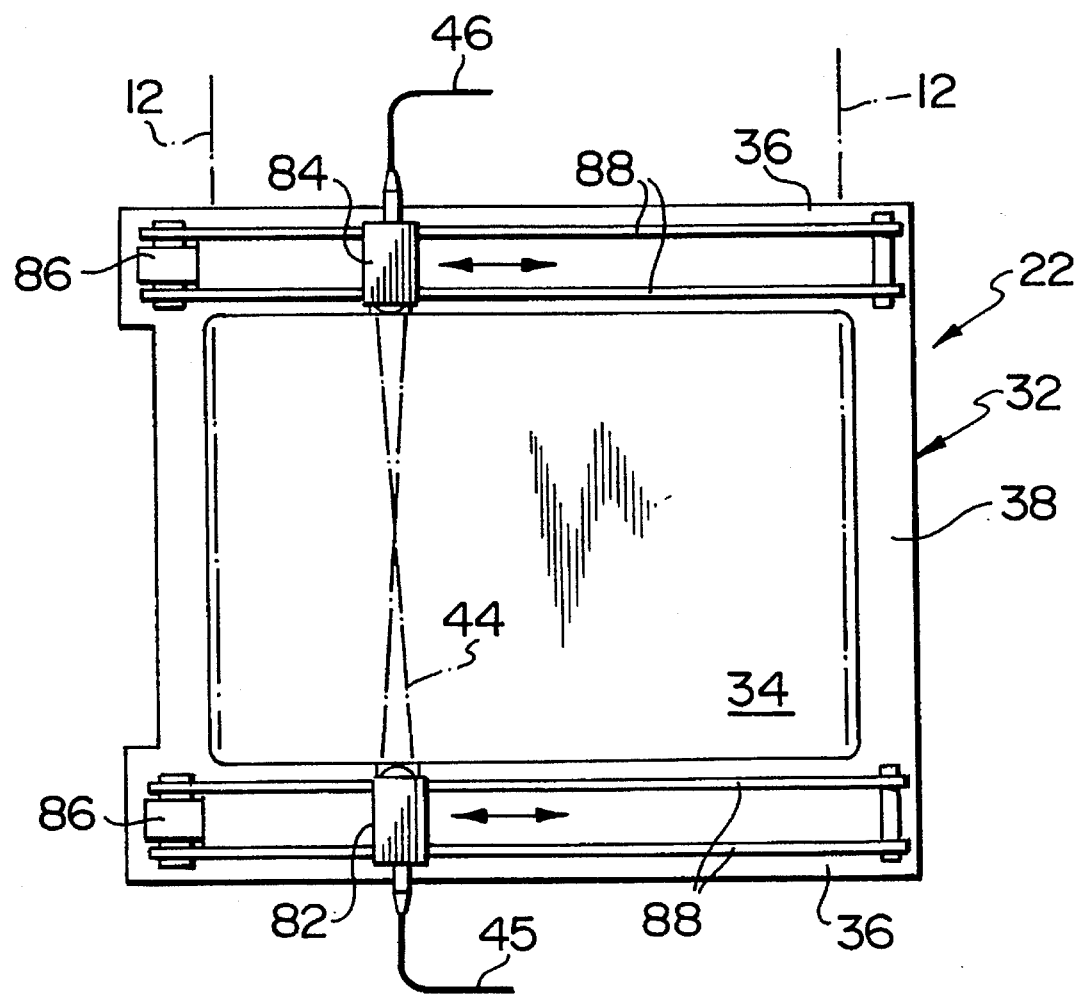

FIG. 5 relates to a second embodiment and is a view taken in the direction of arrow 'V' in FIG. 1 and represents a change to the first embodiment;

FIG. 6 is a view similar to FIG. 5 of part of an apparatus according to a third embodiment and;

FIG. 7 is a view similar to FIG. 2 of the monitoring means in apparatus according to a fourth embodiment.

In a first embodiment as shown by FIG. 1, a wave soldering apparatus 10 is basically of conventional construction in that it has an inclined conveyor 12 moving upwards from left to right in the figure for conveying printed circuit boards 14 through a flux application station 16, past preheaters 18, and then through a wave soldering application station 20.

The first embodiment differs from the basic wave soldering apparatus however in that it includes a monitoring means, designated generally at 22 in FIG. 1 for monitoring the application of flux directed at different positions onto printed circuit boards passing along the conveyor 12. The monitoring means 22 is positioned at a level above a conventional means 24 for directing a wall of flux towards the printed circuit boards 14 moving along the conveyor 12. As shown, the means 24 comprises a conventional rotary drum fluxing construction comprising a rotary perforate drum 26 entering into a chamber 28 so as to be partially submerged in a bath 30 of flux. The rotary drum may be of the type manufactured by Soltec Inc. Within the drum is a conventional means for providing an upward air stream for blowing air through the perforations to carry flux from the drum surface upwards and provide the wall of flux.

The monitoring means, as is more clearly shown in FIG. 2, comprises a rigid rectangular frame 32 defining an opening 34 disposed above the cylinder 26. The opening 34 is provided for enabling a wall 35 of flux (FIG. 1) directed upwardly from the drum 26 to pass through the opening 34 so as to contact the undersides of printed circuit boards 14 passing through the flux application station. The frame 32 provides a means for supporting a means provided for transmitting and receiving infrared light as will be described, the frame 32 having two parallel beams 36 spaced apart in the direction of the passline to define the opening 34. the beams 36 extending transversely of the passline and being connected by side members 38 of the frame. The relative positions of the frame 32 and of the conveyor 12 are shown by the chain-dotted positions for the lateral sides of the conveyor 12 in FIG. 2. The means for transmitting infrared light through the wall 35 of flux comprises a plurality, namely three, of fiber optic launch and lens assemblies 40 (for instance as made by Terra Hertz Inc. of Oriskiny, N.Y.), the assemblies 40 being located in fixed positions spaced apart along one of the beams 36. The means for receiving the infrared light which has passed through the wall of flux and is unabsorbed thereby comprises three receiving assemblies 41 which are similar to the launch assemblies 40 and are disposed upon the other beam 36. The assemblies 40 are positioned such that each assembly is located with its lens 42 accurately aligned with a lens 43 of a corresponding assembly 41 on the opposite beam. The lenses 42 are focusing lenses for focusing the light at a position midway through the wall of flux between the two beams 36, the unabsorbed light then being divergent as it extends towards the corresponding lenses 43 on the other side of the wall. The focused light is indicated by reference 44 in FIG. 2. The monitoring means also includes an optic cable 45 for transmitting the infrared light to each assembly 40 on one beam and another optic cable 46 for receiving the light from the corresponding assembly 40 on the other beam. Only certain optical fiber cables are manufactured which may be used at the present time for transmitting infrared light signals. Such cables incorporate zinc fluoride fibers and are made by Terra Hertz Inc. (referred to above) or alternatively by Galileo Fiber Optics.

Figure 3:
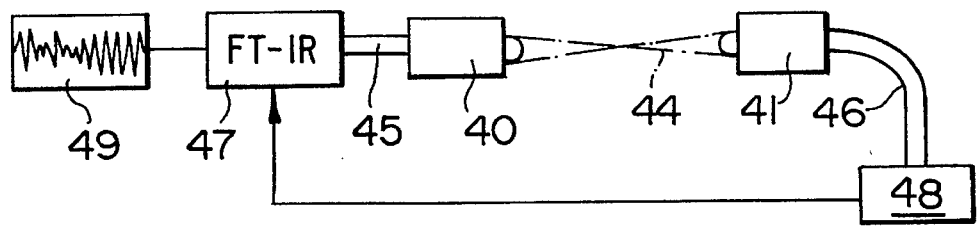
FIG. 3 is a diagrammatic view showing the operation of a monitoring means for measuring the quantity of flux applied to boards passing through the apparatus.
Figure 4:
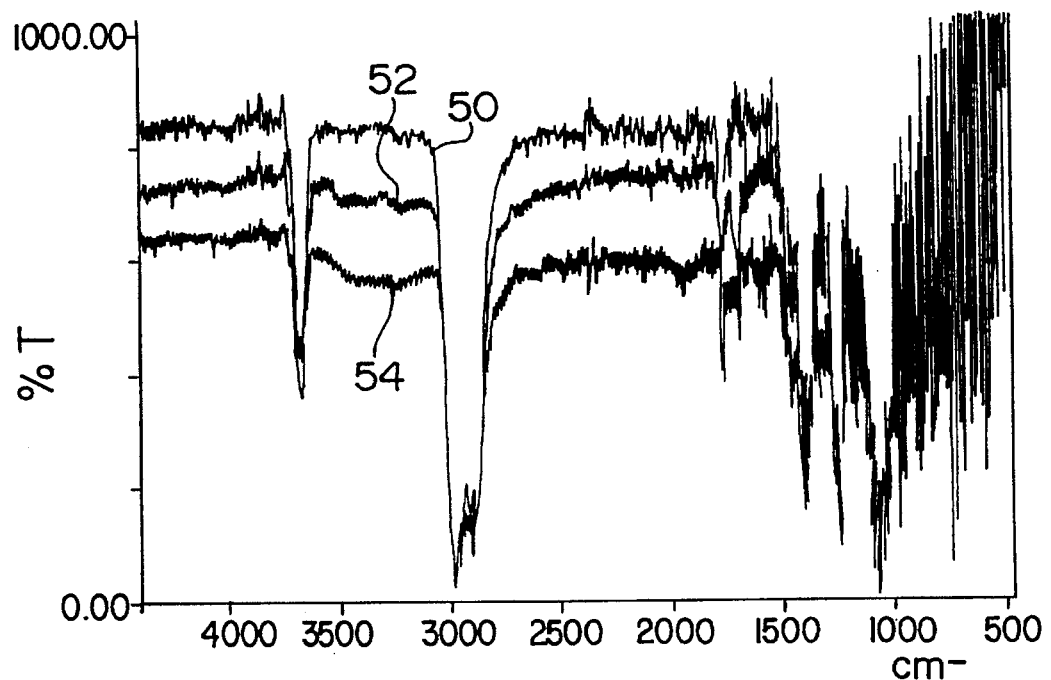
FIG. 4 is a representation of a visual readout of concentration of materials in flux being applied to different positions across the passline for printed circuit boards in the apparatus.

As shown by FIG. 3, the optical fiber cable 45 from each of the transmission fiber optic launch and lens assemblies 40 commences at a source of infrared light which is a Fourier transform-infrared analyzer 47 (referred to herein as "FT-IR"). Signals received by the other assemblies 41 are transmitted by cable 46 to a multiplexer 48 (which may be that designated SP 250 by Galileo Fiber Optics), the multiplexer 48 operating to receive signals in repeating order from the three receiving assemblies 41. Signals are then transmitted from the multiplexer to the FT-IR 47 where they are compared with the signals transmitted to the launch assemblies 40. Differences in the different wavelengths of the infrared light transmitted and received by the FT-IR 47 are then shown for each of the receiving assemblies 41 upon a visual monitor 49 for instance as shown by FIG. 4 which represents graphically along the vertical axis the absorption units of the wavelengths of infrared light and along the horizontal axis the actual wavelengths of the light. On the visual readout, three different curves 50, 52 and 54 may be represented simultaneously, each curve representing the differences between the transmitted infrared light and the unabsorbed light received by each of the receiving assemblies 40.

In use of the apparatus of the first embodiment, and as shown by FIG. 1, printed circuit boards 14 having surface mount components 16 held on their undersurfaces preparatory to soldering are passed in sequence by the conveyor 12 through the apparatus 10 on a fluxing and wave soldering process. As each of the boards passes through the flux application station it is treated on its undersurface with a wall 35 of flux which is directed upwardly by the cylinder 26 rotating in known manner within the bath 30 of the flux. This wall of flux is approximately 4 inches in thickness measured in the direction of the passline of the printed circuit boards. During the application of the flux to the printed circuit boards, infrared light is continuously transmitted from each of the transmitting assemblies 40 (FIGS. 2 and 3), through the wall of flux to be received by the receiving assemblies 41 on the opposite side of the wall. In each case, the infrared light is focused as discussed above so that in passing through the wall, the light energy which is lost is minimized and is capable of being easily received by the lenses 43 on the opposite side of the wall, the distance between the two lenses 41 and 43 being in the order of approximately 10 inches. The transmitting and receiving lenses 41 and 43 are disposed at such a great distance apart to minimize any possibility of flux being deposited upon the lenses.

In each focused beam of light 44 transmitted, as it passes into and through the wall of flux, infrared light in its different wavelengths is absorbed to a degree which is dependent upon the quantities of the different materials in the flux at that particular location in the wall. As a result therefore, unabsorbed light being received at each of the receiving assemblies 41 is correspondingly affected. The cables 46 transmit signals from the unabsorbed light to the multiplexer 48 which then retransmits the signals to the FT-IR 47. The signals received by the FT-IR 47 and representing the unabsorbed light at each of the locations, are then compared with the signals of the different wavelengths of the infrared light which is being transmitted through the cables 45. This comparison is then transmitted to the visual monitor. In each of the curves 50, 52 and 54 on the visual monitor, wavelengths of the infrared light are shown on the horizontal axis and extend from 500 to approximately 4500 Hz. The vertical axis represents the absorption units of each of the wavelengths of infrared light which has been absorbed by the wall of flux. It is thus possible to monitor the quantities of flux constituents on a continuous basis by use of the visual monitor. If a problem is found to exist with the concentration in the flux at any of the locations across the passline by the positions of beams 44, then operation of the apparatus may be ceased immediately to enable a correction to be made to the flux concentration. Hence, as correction may be made to flux concentration almost immediately after a variation away from the concentration requirements occurs, then only a minimal amount of printed circuit boards may be affected by this problem. It follows therefore that the lengthy test periods upon finished printed circuit boards are avoided together with the accompanying wastage of substandard printed circuit boards.

In a second embodiment, which is otherwise similar to that of the first embodiment, means is included in the apparatus for adjusting the flux concentration to any of a chosen plurality of locations laterally of the passline. In this second embodiment as shown by FIG. 5, the means for providing the upward air stream within the drum 26 is replaced by means for providing a plurality of upward air streams in series axially of the drum. These air streams are provided by a means for effecting a change in flux concentration at any of a plurality of locations corresponding, laterally of the passline, to the locations of the launch assemblies 40 and their receiving assemblies 41. In this embodiment, therefore, there are three upward air streams provided by three air flow spray outlets 60, 62 and 64. The outlets are connected to three air flow tubes 66, 68, 70 connected one to each outlet 60, 62 and 64 and a valve 72 is provided in each tube to connect and disconnect each air flow outlet with a source of pressurized air (not shown). Each valve 72 is controlled (e.g. by a solenoid) from the FT-IR 47.

In use, the amount of air flow through each outlet 60, 62 and 64, which then passes upwards through the perforations in the drum 26, controls the quantity of flux which is blown upwards from the drum by the air flow in formation of the wall of flux. If any of the signals reaching the FT-IR 47 indicates that the flux concentration at any of the beam 44 locations is outside the desirable limits then a signal is sent from the FT-IR to operate the solenoid for the particular valve 72 for delivering the air to the corresponding outlet 60, 62 or 64 for increasing or decreasing the pressurized air from the outlet to achieve the desired flux concentration at that location. With the use of apparatus of this kind, the mere monitoring of the flux concentration in the wave soldering apparatus is unnecessary as automatic adjustment of flux concentration occurs automatically. As a result, the flux concentration may be controlled so as not to result in any substandard printed circuit board and surface mount component constructions.

In a third embodiment, a wave soldering apparatus (not shown) is provided which is similar to the first embodiment, except that the drum 26 is omitted. Instead (FIG. 6) a flux spray system is provided which comprises three flux spray heads 74, 76 and 78 located beneath the passline and disposed in series laterally of the passline to provide the single wall of flux directly upwardly towards the conveyor 12. The spray heads 74, 76 and 78 each correspond in lateral position to that of an individual launch assembly 40 and its corresponding receiving assembly 41. The flow of flux through each of the heads 74, 76 and 78 is controlled by an individual valve 80. Each valve 80 is operated by signals received from the FT-IR 47 when it is determined the flux concentration at its corresponding location is outside desirable limits. The valve is then adjusted to adjust the flow of flux through its head 74, 76 or 78 to achieve the desired flux concentration at that location in the wall.

In a fourth embodiment (FIG. 7) which is otherwise similar to the first embodiment, the three launching assemblies 40 and the three receiving assemblies 41 are replaced with one launch assembly 82 and one receiving assembly 84, these two assemblies being mounted one on each of the beams 36 for reciprocal sliding movement upon the beams. The two assemblies 82 and 84 are maintained with their lenses in strict alignment for transmitting and receiving infrared light by being reciprocally drivable across the frame 32 by computer controlled stepper motors 86 drivably connected to an endless drive 88 to which the assemblies 82 and 84 are secured. In use, as the assemblies 82 and 84 are reciprocated continuously across the frame 32, visual readouts are provided on a continuous basis from an infinite number of locations across the feedpath for the printed circuit boards. Should the flux concentration at any location depart from that required, it is immediately noticeable from the readout whereby the apparatus may be stopped immediately for flux concentration changes to take place.

What is claimed is:

1. A method of fluxing and soldering terminals on a printed circuit board comprising:

moving the printed circuit board along a passline through a flux application station while directing a wall of flux across a surface of the board;

in each of a plurality of locations spaced laterally of the passline, passing infrared light having a range of wavelengths, through the wall of flux to cause different wavelengths of the infrared light to be absorbed at least partially by different materials in the flux;

receiving the unabsorbed infrared light which has passed through the wall at each of the locations;

for each location, generating signals corresponding to the different wavelengths of unabsorbed infrared light at that location to enable a determination to be made of the flux concentration at that location;

and moving the board carrying the flux on said surface towards and through a solder application station to apply solder to the terminals.

2. A method according to claim 1 comprising providing the infrared light transmitted at each location as a focused beam having a focal point within the wall of flux, the beam diverging from the focal point to pass out from the wall.

3. A method according to claim 2 wherein each of the plurality of locations is fixed in position laterally of the passline.

4. A method according to claim 2 wherein the light is transmitted from a transmission position which is moving laterally of the passline whereby there are an infinite plurality of locations, and the unabsorbed light is received at a reception position moving in synchronicity with the transmission position.

5. A method of fluxing and soldering terminals on a printed circuit board comprising:

moving the printed circuit board along a passline through a flux application station while directing a wall of flux across a surface of the board;

in each of a plurality of locations laterally of the passline, passing infrared light having a range of wavelengths through the wall of flux to cause different wavelengths of the infrared light to be absorbed at least partially by different materials in the flux;

receiving the unabsorbed infrared light which has passed through the wall at each of the locations;

for each location, generating signals corresponding to the different wavelengths of unabsorbed light at that location and thus corresponding to the actual flux concentration at that location, and when the signals differ from a datum signal which corresponds to the desired flux concentration at that location, effecting a change in flow of flux to change the actual flux concentration towards that desired;

and moving the board carrying the flux on said surface towards and through a solder application station to apply solder to the terminals.

6. A method according to claim 5 comprising creating the wall of flux by rotating a perforate drum about a horizontal axis partly submerged within a bath of the flux so that the flux covers the drum outer surface as the drum surface rotates out of the bath, passing pressurized gas axially into the drum and causing the gas to issue inside the drum from the plurality of axially spaced orifices within the drum, the gas flowing through the perforate drum to raise the flux on the drum outer surface to form the wall of flux; and when the signals at any location differ from the datum signal, effecting a change in pressure of the gas flowing from at least one of the orifices corresponding laterally of the passline to said location thereby changing the flow of gas at said location through the drum and changing the actual concentration of flux towards that desired.

7. A method according to claim 5 comprising providing the infrared light transmitted at each location as a focused beam having a focal point within the wall of flux, the light diverging from the focal point to pass out from the wall.

8. A method according to claim 7 wherein each of the plurality of locations is fixed in position laterally of the passline.

9. A method according to claim 7 wherein the light is transmitted from a transmission position which is moving laterally of the passline whereby there are an infinite plurality of locations, and the unabsorbed light is received at a reception position moving in synchronicity with the transmission position.

10. A wave soldering apparatus comprising:

a flux application station, and a solder application station disposed downstream of the flux application station along the passline for printed circuit boards to be passed through the apparatus;

means for creating a wall of flux in the flux application station and for directing it upwardly towards the passline to coat with flux printed circuit boards as they move through the application station;

means for passing infrared light at a plurality of locations spaced laterally of the passline through the wall of flux and means for receiving infrared light which is unabsorbed by the materials of the flux in the wall and which has passed through the wall, the infrared light having an operating range of wavelengths;

and means for generating signals corresponding to the different wavelengths of unabsorbed infrared light at each of the plurality of locations to enable a determination to be made of the flux concentration at that location.

11. Apparatus according to claim 10 wherein the means for transmitting infrared light and for receiving infrared light at each location comprises transmitting and receiving lenses, a transmitting lens provided to focus a beam of infrared light to a focal point within the wall of flux on the receiving lens is provided to receive unabsorbed infrared light in the form of a diverging beam from the focal point.

12. Apparatus according to claim 10 wherein means is provided for reciprocally transversing beneath the passline the means for transmitting the infrared light and the means for receiving the unabsorbed infrared light with the means for transmitting the infrared light and the means for receiving the unabsorbed infrared light moving synchronously to maintain reception for the receiving means of the unabsorbed light.

13. Apparatus according to claim 10 wherein at each of the plurality of locations there is disposed means for transmitting infrared light and for receiving the unabsorbed infrared light, and the means for transmitting and receiving at each location is spaced laterally of the passline from the means for transmitting and receiving at each other location.

14. Apparatus according to claim 13 wherein a support means is provided extending laterally of and beneath the passline, the support means carrying the means for transmitting infrared light and the means for receiving the unabsorbed infrared light.

15. Apparatus according to claim 14 wherein the support means comprises two beams extending laterally of the passline, the beams spaced apart in the direction of the passline to provide a space for the upward direction of the wall of flux.

16. Apparatus according to claim 15 wherein each of the means for transmitting infrared light and each of the means for receiving unabsorbed infrared light is adjustably mounted in position laterally of the passline.

17. A wave soldering apparatus comprising:

a flux application station, and a solder application station disposed downstream of the flux application station along a passline for printed circuit boards to be passed through the apparatus;

means for creating a wall of flux in the flux application station and for directing the wall of flux upwardly towards the passline to coat with flux printed circuit boards moving through the application station;

means for adjusting the flux concentration to any of the plurality of locations spaced laterally of the passline;

means for transmitting infrared light through the wall of flux at each of the plurality of locations and means for receiving infrared light which is unabsorbed by the materials of the flux in the wall and which has passed through the wall, the infrared light having an operating range of wavelengths;

means for generating signals corresponding to the different wavelengths of unabsorbed light at each of the locations, the generated signals also corresponding to actual flux concentrations at that location;

and means to effect a change in the flux concentration at any of the locations towards a desired flux concentration when a generated signal at that location differs from a datum signal which corresponds to the desired flux concentration.

* * * * *